United States Patent [19]

You

[11] Patent Number: 5,362,630
[45] Date of Patent: Nov. 8, 1994

[54] ISOLATION OF PSEUDOMONAS SALICYLATE HYDROXLASE AND ITS USE FOR THE IDENTIFICATION AND QUANTITATION OF SALICYLATE IN BODY FLUIDS

[75] Inventor: Kwan-sa You, Durham, N.C.

[73] Assignee: Duke University, Durham, N.C.

[21] Appl. No.: 895,424

[22] Filed: Jun. 5, 1992

Related U.S. Application Data

[63] Continuation of Ser. No. 713,586, Jun. 11, 1991, abandoned, which is a continuation of Ser. No. 404,664, Sep. 8, 1989, abandoned, which is a continuation of Ser. No. 500,800, Jun. 7, 1983, abandoned, which is a continuation of Ser. No. 287,802, Jul. 28, 1981, abandoned.

[51] Int. Cl.$^5$ ............ C12Q 1/26; C12N 9/02
[52] U.S. Cl. ............ 435/25; 435/4; 435/189; 435/817; 435/874; 435/877
[58] Field of Search ............ 435/4, 25, 189, 805, 435/810, 817, 874–877; 422/55, 57

[56] References Cited

U.S. PATENT DOCUMENTS

| | | | |
|---|---|---|---|
| 3,954,412 | 5/1976 | Ogawa et al. | 422/56 |
| 4,189,536 | 2/1980 | Green | 435/17 X |
| 4,416,983 | 11/1983 | Röder et al. | 435/25 |
| 4,777,132 | 10/1988 | Green et al. | 435/25 |

OTHER PUBLICATIONS

Clinical Chemistry, vol. 30, No. 9 (1984), pp. 1549–1551, Quantification of Salicylate in Serum by use of Salicylate Hydroylase.
Clinica Chimica Acta, 149 (1985), pp. 281–284, Polarographic Quantification of Salicylate in Serum by Salicylate Hydroxylase.
J. Bauer, Clinical Laboratory Methods Ninth Edition (The C. V. Mosby Company 1982), "Salicylates" pp. 633–634.
Kamin et al "Salicylate Hydroxylase" in Methods in Enzymology vol. LIII (Academic Press 1978) pp. 527–543.
Bergmeyer, Methods of Enzymatic Analysis vol. 1 (Academic Press 1976) pp. 103–107.
Richterich, Clinical Chemistry: Theory and Practice (Academic Press 1969) pp. 289–290.
Yamamoto et al., "Salicylate Hydroxylase, a Monooxygenase Requiring Flavin Adenine Dinucleotide" in J. Biol. Chem. vol. 240 (1965) pp. 3408–3413.
You et al, "Quantitation of Salicylate with Purified Psuedomonas Salicylate Hydroxylase", *Clin. Chem*, vol. 27, No. 6, Abstract No. 419, Jun. 1981.
Gupta et al, "Salicylate Hydroxylase Free of NADH Oxidase from *Pseudomonas*", Clinical Chemistry, vol. 32, No. 6, p. 1061 (1986).
Hamzah et al, "Determination of the Position of Monooxygenation in the Formation of Catechol Catalyzed by Salicylate Hydroxylase," *The Journal of Biological Chemistry*, v. 256, No. 12, pp. 6392–6394, 1981.
Morris et al, "Development of . . . Enzyme–Mediated Colorimetric Assay of Silicylate in Serum", *Clinical Chemistry*, vol. 36, No. 1, pp. 131–135 (1990).
You et al, "Affinity Chromatography of *Pseudomonas* Salicylate Hydroxylase", *Analytical Biochemistry*, 114, 177–185 (1981).

*Primary Examiner*—Toni R. Scheiner
*Attorney, Agent, or Firm*—Oblon, Spivak, McClelland, Maier & Neustadt

[57] ABSTRACT

Salicylate hydroxylase isolated from Pseudomonas bacteria can be used to determine the level of salicylate in a body fluid by reacting a sample of the fluid with the enzyme and monitoring the conversion of salicylate to catechol. A method of purifying the enzyme from crude bacterial extract using a salicylate affinity column is also disclosed.

15 Claims, 10 Drawing Sheets

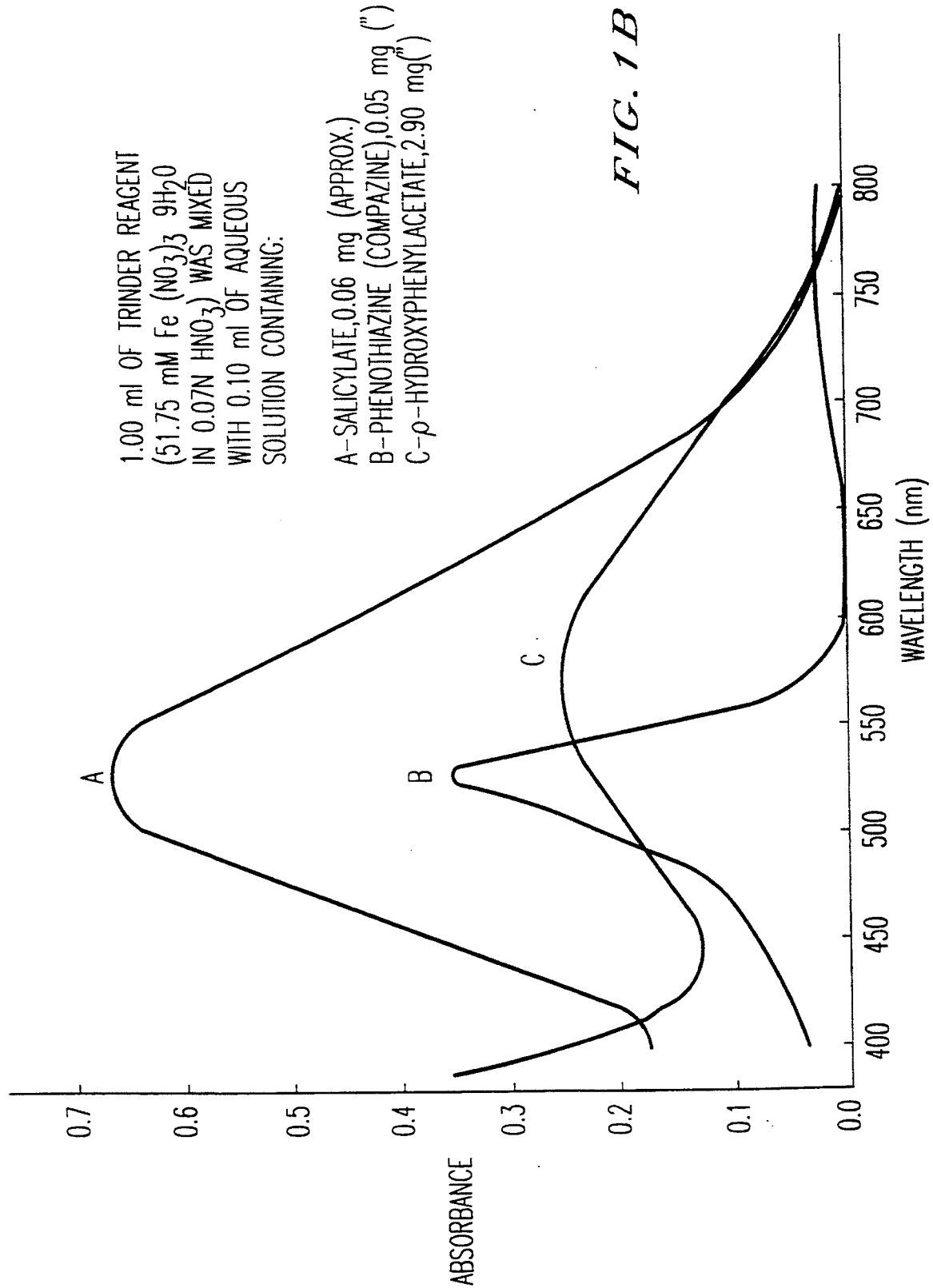

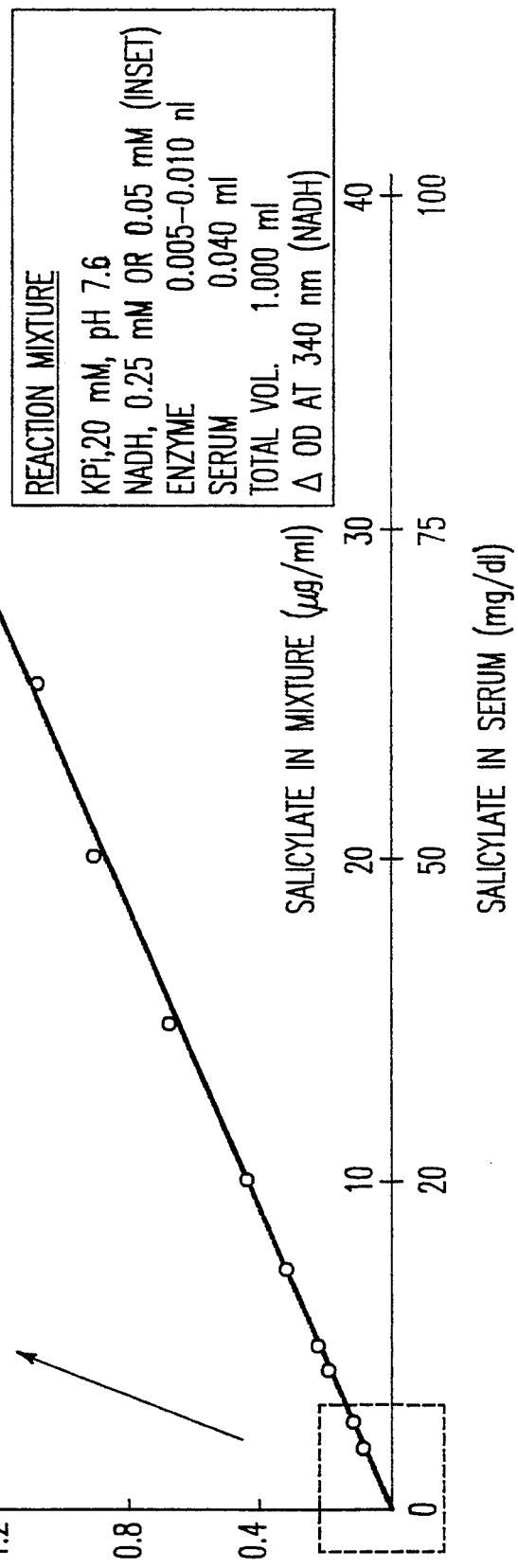
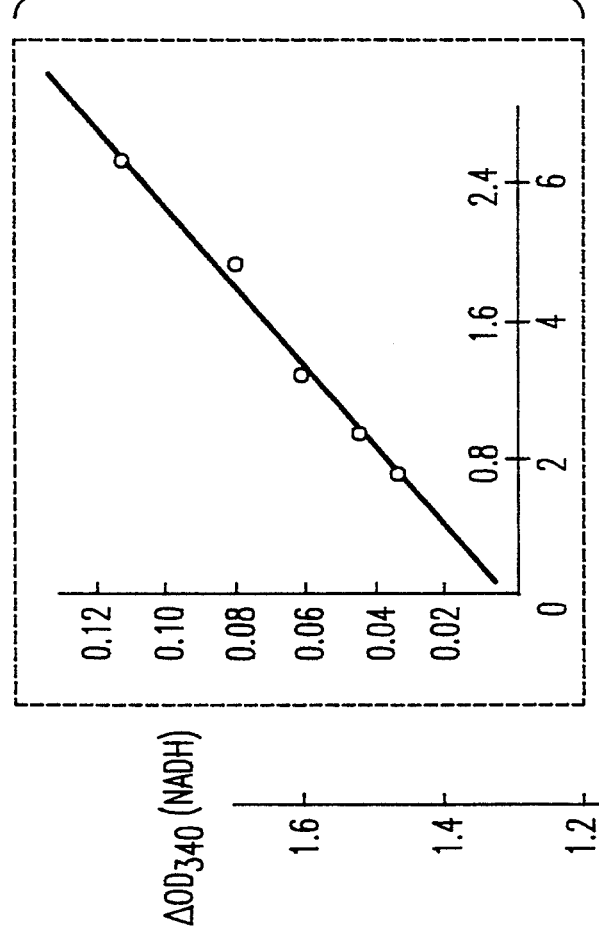
FIG. 6A
FIG. 6B

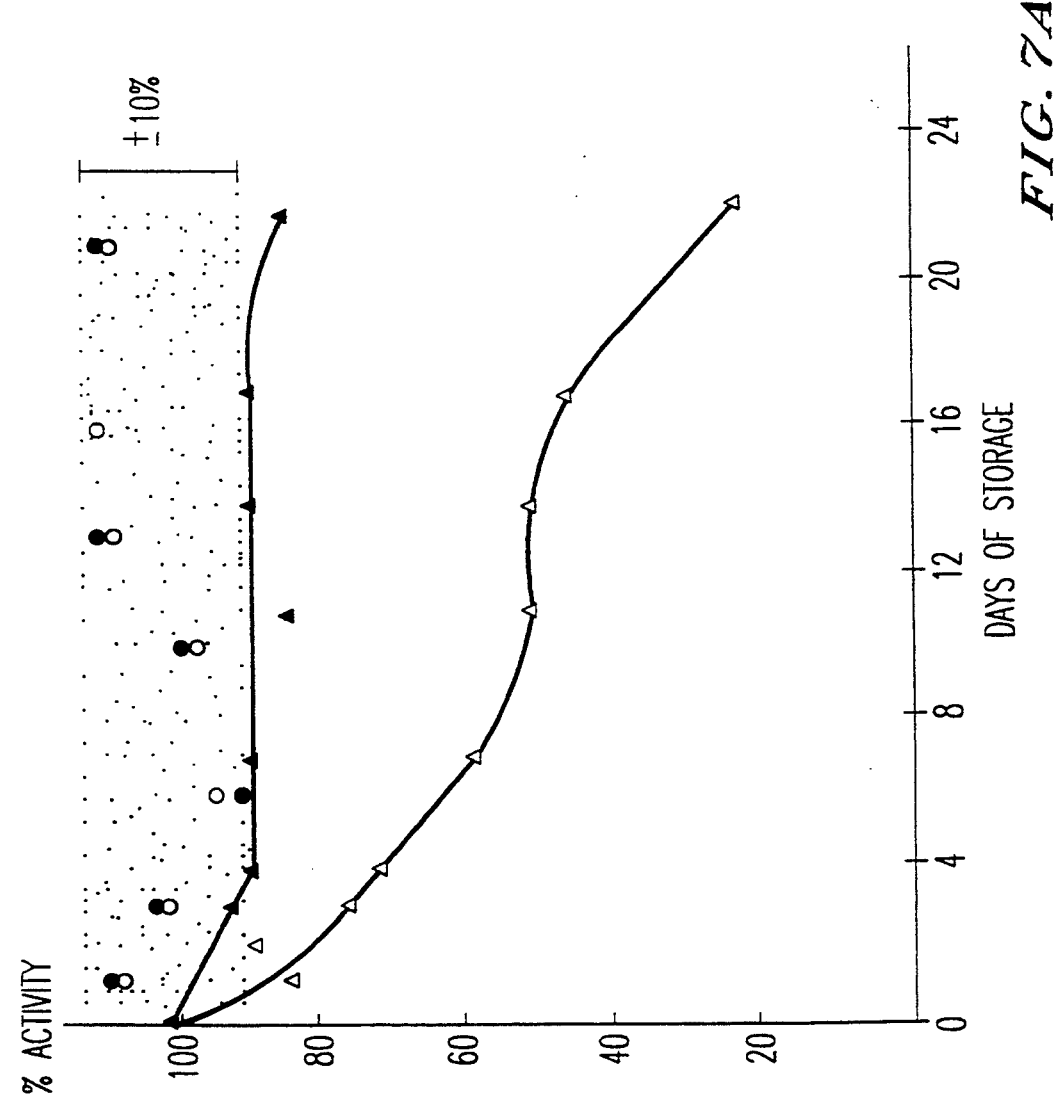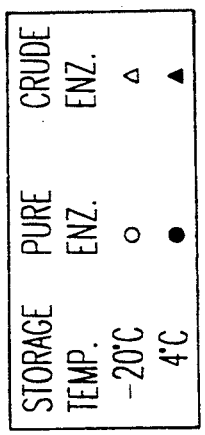

ISOLATION OF PSEUDOMONAS SALICYLATE HYDROXLASE AND ITS USE FOR THE IDENTIFICATION AND QUANTITATION OF SALICYLATE IN BODY FLUIDS

This application is a continuation of application Ser. No. 07/713,586, filed on Jun. 11, 1991, now abandoned, which is an FWC appl. of Ser. No. 07/404,664, filed on Sep. 8, 1989, now abandoned which is a continuation of Ser. No. 06/500,800, filed on Jun. 7, 1983, now abandoned, which is a continuation of Ser. No. 06/287,802, filed on Jul. 28, 1981, now abandoned.

BACKGROUND OF THE INVENTION

1. Field of the Invention

The present invention relates to a new method of isolating salicylate hydroxylase from Pseudomonas bacteria and to methods of using this enzyme for the identification and quantitation of salicylate in body fluids.

2. Description of the Prior Art

The unique property of controlling pain, fever, and inflammation has made acetylsalicylic acid (aspirin) one of the most widely used drugs today. However, its frequent use and easy availability also have made it the cause of more cases of accidental poisoning in children than any other substance.

When aspirin is ingested, it ionizes and rapidly loses its acetyl group to become salicylate. Therefore, what is monitored in aspirin therapy or intoxication is salicylate; aspirin itself is analyzed seldomly because its level in patients has little clinical significance. In order for aspirin treatment to be effective, serum or plasma levels of salicylate must be kept within the therapeutic range (5-40 mg/dl serum/plasma). If aspirin is present in an overdose (over 45 mg/dl serum/plasma level), the resulting high level of salicylate acts as a serious poison often causing coma and death.

Since salicylate intoxication occurs frequently, it would be very useful to develop a simple, quick, and specific method for identification as well as quantitation of salicylate in patients who are taken to an emergency room for an overdose of an unknown drug. Such a method would also be valuable in routine monitoring of salicylate levels in those patients who require continuous aspirin therapy. Unfortunately, no test having all the desirable characteristics now exists.

Presently, the most popular analytical methods for salicylate are gas chromatography (GC), liquid chromatography (LC), and the Trinder method. Because of several obligatory steps, such as deproteinization, extraction, derivatization, and column regeneration, that must be carried out for each analysis, GC and LC are laborious and time consuming. As such, they are not the methods of choice in an emergency situation when quick identification of the poison followed by proper treatment is essential. In addition, they require expensive instruments (which are also costly to maintain) and specially trained technicians.

The Trinder method, which is based on the development of a purple color as a result of the reaction between $Fe^{+++}$ and compounds having an enolizable hydroxyl group, such as phenols (salicylate is a phenol), is simple and relatively quick but, unfortunately, is not salicylate-specific. Thus the Trinder test is severely interfered with not only by hundreds of phenols but also by compounds like acetoacetate (found in diabetic patients). In addition, phenothiazines, which have intoxicating incidents slightly more frequent than salicylate, give a color that can be easily mistaken for that caused by salicylate. In fact, the same ferric reagent can be employed for the detection of both salicylate and phenothiazines. The spectra of several products of the Trinder reaction with compounds that interfere with the quantitation of salicylate are shown in FIGS. 1A) and B). Because of these frequent false-positive reactions, the Trinder method is always accompanied by the danger of misdiagnosis.

Furthermore, the Trinder method often give irrational results if the serum/plasma salicylate concentration is below 10 mg/dl. The serum from a patient who never received salicylate often shows a salicylate level as high as 10 mg/dl. Such irrational results are most likely due to turbidity caused by serum proteins under acidic condition (the Trinder reagent is made in HCl, $HNO_3$, or $H_2SO_4$). The manufacturers of the Trinder reagent claim that the turbidity can be removed by centrifugation at 3,000 rpm for 10 minutes. In the experience of the present inventor, however, slight turbidity remains after centrifugation at this speed when a centrifuge of the type commonly available in toxicology and clinical laboratories is used (Table-top type). Complete removal of the turbidity can be achieved if centrifugation is carried out at a 100,000xg for 15 minutes, but centrifuges capable of the requisite high speeds are less common in the clinical laboratory. Some medical centers formerly employed the Trinder method but, because of persistent inconsistent results, now extract salicylate with ethylene dichloride from serum before subjecting the serum to the Trinder test; addition of the extraction step makes the Trinder test no longer a fast method and its greatest advantage is lost.

Another desirable feature for a new salicylate test method would be compatability with an automatic analyzer. Many toxicology and clinical chemistry laboratories which handle large numbers of samples are equipped with automatic analyzers. No method currently available can use these analyzers for accurate salicylate determinations because of the turbidity problem. Adoption of the Trinder method to auto analyzers is possible if the most time consuming step, namely removal of the turbidity by centrifugation or by filtration, is performed manually. However, if this step is carried out manually, it is senseless to use an automatic analyzer since manual determination of the absorbance of the clarified samples by a spectrophotometer is simpler and less expensive. It should also be pointed out that the use of the Trinder reagent in an expensive automatic analyzer is risky since the reagent is corrosive and contains high concentrations of heavy metals such as Fe and Hg or W; contamination of the expensive instrument by these metals would cripple the analyzer's functions that involve enzymes because even trace amounts of these metals often serve as potent inhibitors of many enzymes.

In 1970, White-Stevens and Kamin reported the purification and properties of salicylate hydroxylase (salicylate 1-monooxygenase EC 1.14.13.1) from a soil microorganism (Biochem. Biophys. Res. Commun. 38, 882–889 (1970)) later identified as a Pseudomonas. This enzyme catalyzes the unidirectional conversion of salicylate to catechol in the presence of molecular oxygen and NAD(P)H (nicotinamide adenine dinucleotide or nicotinamide adenine dinucleotide phosphate). Kamin's enzyme is physically as well as catalytically different from the salicylate hydroxylase that was isolated from

*Pseudomonas pupita* and described by Yamamoto et al in Japan five years earlier (J. Biol. Chem., 240, 3408 (1965)). Thus, Kamin's enzyme has a molecular weight of 91,000±3000 and is composed of two apparently identical subunits, each of which contains one FAD (flavin adenine dinucleotide) and can utilize both NADH and NADPH (with the same $V_{max}$) as reductant. On the other hand, the enzyme purified by the Japanese workers is a monomeric protein containing one FAD per molecular mass of 57,200 daltons and does not utilize NADPH. Nevertheless, similarities exist between these enzymes as would be expected for enzymes isolated from bacteria within the same genus that perform the same physiological function. Because these salicylate hydroxylase enzymes require an external reductant (i.e., NADPH or NADH) and only one oxygen atom of the molecular oxygen is incorporated into the substrate as a hydroxyl group during the catalysis, they belong to the class of enzymes known as external flavoprotein monooxygenases.

It would be desirable to have an enzymatic method of determining salicylate levels in body fluids since such a method would be specific for salicylate in the presence of more interfering substances than are now allowed with current test methods and would allow more rapid determination of salicylate level than LC or GC methods. In order to make such a method readily available, it is also desirable to have a method of purifying the chosen enzyme in an adequate yield and to the desired level of activity. However, prior to the present invention, no such methods existed.

SUMMARY OF THE INVENTION

Accordingly, it is an object of this invention to provide a method for the rapid determination of the presence and quantity of salicylate in a body fluid which is not subject to interference by other phenols, acetoacetate, or phenothiazines.

It is a further object of this invention to provide an enzymatic method for the determination of salicylate in a body fluid that is easily carried out in a clinical laboratory and which is adaptable for use in an autoanalyzer without pretreating the sample.

It is a still further object of this invention to provide a method of isolating in good yield and purity an enzyme capable of accomplishing the above objectives.

These and other objects of the invention as will hereinafter become more readily apparent have been accomplished by providing a method of testing for salicylate in a body fluid comprising the steps of reacting a sample of a body fluid with Pseudomonas salicylate hydroxylase and monitoring the conversion of salicylate to catechol and by providing a method of purifying salicylate hydroxylase, comprising the steps of passing a sample containing crude salicylate hydroxylase over an anion exchange material, eluting partially purified salicylate hydroxlase from said anion exchange material, passing said partially purified salicylate hydroxylase over a substrate having a salicylate derivative bound to said substrate so that said salicylate retains affinity for salicylate hydroxylase, and eluting salicylate hydroxylase from said substrate.

BRIEF DESCRIPTION OF THE DRAWING

A more complete appreciation of the invention and many of the attendant advantages thereof will be readily obtained as the same become better understood by reference to the following detailed description when considered in connection with the accompanying drawings, wherein:

FIGS. 1A and 1B show the spectra of several products of the Trinder reaction with compounds that interfere with the quantitation of salicylate;

FIGS. 6A and 6B show the linearity of the data disclosed in FIG. 5;

FIG. 7A and 7B show the stability of salicylate hydroxylase isolated from Pseudomonas sp. RPP when stored at various temperatures and degrees of purity;

DESCRIPTION OF THE PREFERRED EMBODIMENTS

Figure 1A:
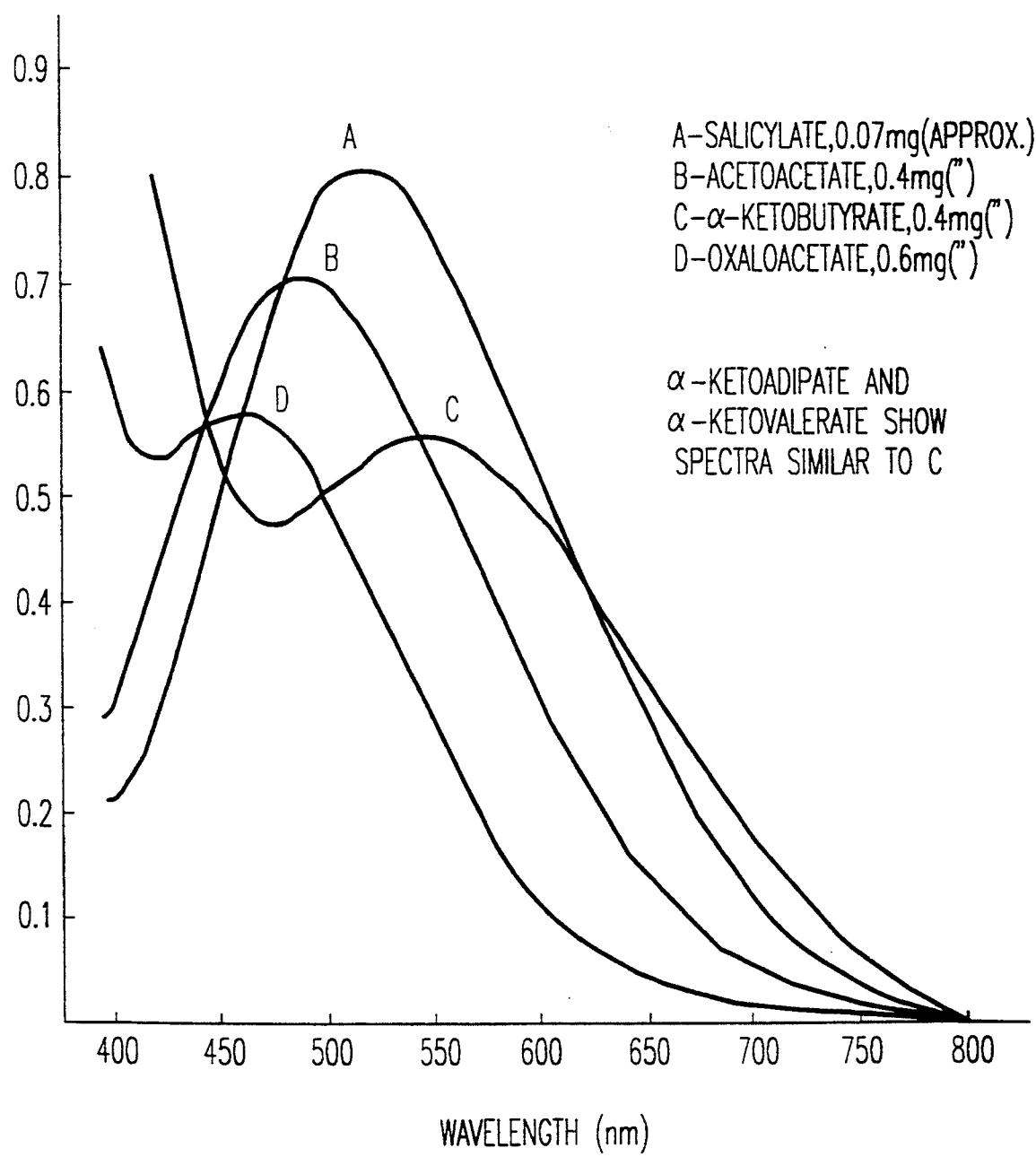

Pseudomonas salicylate hydroxylases have been known for some time as discussed above. However, there does not appear to have been any prior application of these enzymes to clinical analysis. This is not unusual since many enzymes are not suitable for use in the clinical laboratory. Only after testing for stability, reproducibility, reliability, lack of interfering substrates, and adaptability to standard techniques can an enzyme be said to be suitable. The present invention came about as a result of investigations of the enzyme disclosed and described by White-Stevens and Kamin in Biochem. Biophys. Res. Commun., 38, 882 (1970). The isolation of this enzyme was reported in J. Biol. Chem., 247, 2358 (1972). Both of these articles are hereby incorporated by reference.

The term "salicylate enzyme" or "hydroxylase" or "enzyme" in this application, unless otherwise qualified refers to a salicylate hydroxylase derived from a Pseudomonas bacterium. A salicylate hydroxylase enzyme can be induced in a bacterial culture of Pseudomonas by growing the culture in a medium having salicylate as the sole carbon source. Any species and strain of Pseudomonas that survives under these conditions will produce salicylate enzyme, but, of course, the amount produced will vary from species to species and strain to strain. Not all of the enzymes produced in this manner will have the same complete amino acid sequences and physical characteristics as indicated by the differences between the Kamin and Yamamoto enzymes, but all salicylate hydroxylase enzymes produced in this manner are considered to be within the scope of the invention unless otherwise indicated. Preferred species of Pseudomonas are those that produce salicylate hydroxylase in high yield. Particularly preferred are Pseudomonas sp. RPP (ATCC 29351), Pseudomonas sp. RWS (ATCC 29352), and *Pseudomonas pupita*, which is described in Yamamoto et al, J. Biol. Chem., 240, 3408 (1965), which is hereby incorporated by reference.

The procedures for inducing the enzyme in a bacterium and for producing a crude enzyme extract are disclosed in detail in the J. Biol. Chem. article by White-Stevens and Kamin incorporated above and are summarized in the following paragraphs. Induction of enzymes in bacteria is well known and is not considered to be part of the present invention.

A Pseudomonas bacterium is maintained and subcultured in a liquid basal medium containing sodium salicylate or a different salicylate salt as the sole carbon source. The medium is buffered and contains other essential ingredients for growth, such as a nitrogen source, co-factors, vitamins, and other ingredients necessary for the growth of the bacterium being cultured. A typical medium might contain (in addition to sodium salicylate) $KNO_3$, $K_2HPO_4$, $KH_2PO_4$, $MgSO_4$, $CaCl_2$, riboflavin, EDTA (ethylenediaminetetracetic acid, often as the tetra sodium salt), $ZnSO_4$, $FeSO_4$, $MnSO_4$, $CaSO_4$, $CoSO_4$, $Na_2B_4O_7$, and $(NH_4)_6Mo_7O_{24}$, plus sufficient $H_2SO_4$ to retard precipitation.

The bacterium can be cultured in any size vessel, 20- to 6.00- liter carboys or fermenters being well suited for large scale production. Temperature need not be controlled precisely, although growth is generally more rapid within the range from 5° C. to 38° C. and temperature control within this range is preferred. Preferred is culturing from 25° C. to 37° C., with culturing at about 37° C. being most preferred. Bacterial growth is generally vigorous at 37° C. The pH should be maintained in the pH range from 6.5 to 8.9 in order to maximize enzyme production although some enzyme is produced at other pH values. A pH of about 7.6 is most preferred. The pH of the medium generally rises when salicylate is consumed during the culturing process. Any non-toxic inorganic or organic acid such as, for example, HCl, or base, such as, for example, $Na_2CO_3$ may be used to adjust the pH. Although pH control is not essential in order to obtain at least some enzyme, pH control is essential for maximum induction of 1.

Salicylate concentrations above 0.2% inhibit bacterial growth so that the salicylate level is preferably maintained between 0.02 and 0.2%. Enzyme yield is generally low if the salicylate concentration falls below 0.03%. The level of salicylate concentration may be measured by monitoring the absorbance of light by salicylate anywhere in the range of 290–305 nm although monitoring at about 296 nm is preferred.

The bacteria can be harvested either continuously or in batches by centrifugation or filtration, with replacement of nutrient as needed. The collected cell paste may be used immediately, or it may be frozen and stored for up to several years.

Cell paste (thawed if from frozen cell paste) is suspended in a suitable buffer (e.g. potassium phosphate buffer, pH 7.6, hereafter abbreviated KPi, pH 7.6) and the cell walls are disrupted to release the enzyme. An homogenizer may be used initially to break up cell clumps if desired. The method used to disrupt the cell is not restricted as long as the enzymes released into the suspension medium are not destroyed. Suitable methods include grinding or blending the cells in the presence of glass beads, rupturing the cells in a French press, and freeze-thawing the cells. Particularly suitable is sonication. The resulting crude extract is centrifuged or filtered to remove cell debris, and the supernatant or filtrate is used in succeeding steps of enzyme purification.

Salicylate hydroxylase was purified at a yield of 22.5% by White-Stevens and Kamin, who employed protamine sulfate fractionation, ammonium sulfate fractionation, and ion-exchange chromatography, and gel filtration. They lost about half of the enzyme activity during protamine sulfate treatment and more at the ammonium sulfate fractionation step.

In order to facilitate the purification process of the enzyme and, at the same time, to increase the final yield, several affinity chromatographic procedures were attempted before the present method was discovered. It is well known that many NADH/NADPH-requiring enzymes bind to 8-(6-aminohexyl)amino-ATP-SEPHAROSE and to Cibacron Blue F3GA. Pseudomonas salicylate hydroxylase showed, however, very weak affinity toward the ATP (adenosine triphosphate) ligand (both in the absence and presence of NADH) and no affinity at all toward the Cibacron Blue gel. It was therefore concluded that these two ligands were not useful for the purification of salicylate hydroxylase.

The investigations leading to the present invention centered on affinity chromatography using a salicylate ligand combined with anion exchange chromatography.

In order to prepare an affinity chromatography column, a salicylate analogue may be bound to a substrate (solid matrix) in any way so long as sufficient binding affinity for the salicylate enzyme is maintained. The most preferred salicylate analogue is salicylate itself, with the only substitution occurring at the position of attachment. Other substitution is permissible so long as at least 10% of the binding affinity of the enzyme for unsubstituted salicylate is maintained. Covalent attachment through the 5-position (para to the hydroxyl) or the 4-position (para to the carboxylate group) is preferred; attachment through the 4-position is most preferred.

Attachment may be accomplished by direct attachment of the substrate to the salicylate ring, but attachment through a bridging group (spacer) is preferred in order to eliminate the steric hinderance between the enzyme molecule and the solid matrix. The bridging group may form a carbon-carbon bond with the salicylate molecule, but attachment by means of a reaction between a reactive functional group in the bridging group and a reactive functional group of a para-substituted salicylate derivative is preferred.

Suitable bridging groups include bifunctional molecules having one functional group capable of reacting with the substrate and a second functional group capable of reacting with the salicylate derivative. Preferred functional groups for forming bonds with the salicylate moiety are those which form amide and ester linkage with amines and alcohols, respectively, such as acid halides and acid anhydrides. Preferred are N-hydroxysuccinimide esters of carboxylic acids. The two reactive functional groups are preferred to be separated by at least three methylene groups or other groups of similar dimensions. Branching is permitted as long as the binding affinity of the salicylate analogue with the enzyme is not reduced to below 10% of that for unsubstituted salicylate with the enzyme. The linking group may be part of a commercial preparation also containing a substrate, such as an agarose bead to which a molecule having a suitable reactive functional group is attached at a distance from the substrate. One example of such a preparation is activated CH-SEPHAROSE 4B, a product of Pharmacia Fine Chemicals. This material consists of SEPHAROSE 4B beads to which the N-hydroxysuccinimide ester of 6-aminohexanoic acid is coupled.

The reactive functional group in the para position of salicylate to which the bridging group becomes attached is preferred to be hydroxyl or amino, either unsubstituted or substituted with one $C_1$-$C_4$ alkyl group; of these —$NH_2$ is most preferred.

A preferred structure for the salicylate analogue-bridging group-substrate complex has the following formula:

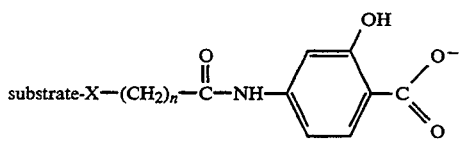

where n=3–6 and X=O or NH.

The substrate to which the affinity ligand is attached may be any porous non-reactive composition having pores large enough to allow passage of proteins without hindering their movement. Suitable substrates include porous glass, agarose, dextran, and cellulose beads. Preferred are agarose beads such as SEPHAROSE 4B, a product of Pharmacia Fine Chemicals. SEPHAROSE is a bead-formed gel formed from agarose, which is a linear polysaccharide that consists of alternating residues of D-galactose and 3,6-anhydro-L-galactose units. The designation 4B refers to the pore size, which gives an exclusive limit for proteins of approximately 10 million.

The affinity column is prepared according to standard practices. The substrate may be first reacted with a bifunctional bridging group so as to leave one reactive function still present in the bridging group, generally at the distal portion of the bridging-group. If necessary, this functional group is converted to a more reactive one (activated) after which reaction between the bridging group and the ligand is allowed to. occur, generally by suspending the substrate-bridging group adduct in a solution of the ligand or by passing a solution of the ligand through a column containing the substrate-bridging group adduct. Aqueous or organic solvents may be used, depending on the chemistry of the react ions involved.

Once the salicylate affinity material has been prepared, it is placed in a suitable column or batch container and a solution containing the salicylate enzyme is passed over the preparation. Aqueous solutions of enzyme are required in order to maintain the active conformational state of the enzyme, but other solutes may be present as needed to preserve or enhance binding. Possible solutes include buffering agents and salts required to maintain proper ionic strength. Preferred are solutions containing buffers and other solutes that maintain physiological conditions normally present in the bacterium from which the enzyme is isolated.

Once the salicylate enzyme has been loaded onto its column, additional solution is added to wash the unbound or weakly bound contaminants from the column. The washing solution may be the same as or different from the solvent used to load the column. Preferred are volumes of washing solutions from 1–10 column volumes with about 5 volumes being most preferred. Preferred washing solutions are 5 to 20 mM KPi at the physiological pH of the enzyme, with 10 mM KPi, pH about 7.6, being most preferred.

After washing off contaminants, the salicylate enzyme may be released from the column by adding any substance or changing any condition so that a temporary change occurs in the conformation of the enzyme and thereby reduces its binding affinity or by providing a soluble salicylate analogue for the enzyme and thereby bringing the enzyme back into solution when the enzyme binds with the soluble salicylate analogue. Examples of added substances to change binding affinity are concentrated solutions of salts having high ionic strength, e.g., >100 mM KPi, pH 7.6. Preferred salicylate analogues are derivatives of benzoate; of these o-hydroxybenzoates are more preferred, with salicylates being most preferred. The salicylate analogue may be added as an acid providing that the pH is adjusted to near neutrality, although water-soluble salts are preferred. The most preferred salts are sodium and potassium salicylate.

The eluted salicylate enzyme may be further purified by passing the effluent from the affinity column through an anion exchange resin. Any of the anion exchange resins having pendant cationic groups at a pH at or near the physiological pH of the enzyme is suitable. Preferred are resins having pendant ammonium groups. Most preferred is a DEAE cellulose (diethylaminoethyl cellulose) derivative such as DE-52 cellulose.

The same solutions may be used to apply the enzyme to the anion exchange column as are disclosed above for the affinity column. After the enzyme is loaded onto the column, the column is washed with a dilute buffered solution until no more protein elutes from the column. Buffers having a pH between 7.0 and 8.9 are suitable. is a potassium phosphate buffer of about 20 mM concentration and a pH of about 8.5. Presence of protein in the eluent can be detected spectrophotometrically at 280 nm.

The enzyme may be removed from the anion exchange column using a linear salt gradient from about 20 to about 200 mM. Potassium phosphate buffer or other buffers of varying concentration are convenient as they allows maintenance of pH at or near requisite value. Preferred is a potassium phosphate buffer gradient at pH 8.5. Fractions from the eluent are collected and those containing salicylate enzyme activity are pooled. Enzyme may be detected by allowing an aliquot of a fraction to react with salicylate in the presence of NAD(P)H, under conditions similar to those described in the following discussion of the use of this enzyme as an analytical reagent. The reaction is followed by spectrophotometrically monitoring the absorbance decrease at 340 nm (disappearance of NAD(P)H) or 296 nm (disappearance of salicylate).

Although affinity chromatography may be followed by anion exchange as described above, the reverse order is preferred. Similar yields are expected for either order of steps, but anion exchange as a first step allows the salicylate affinity columns to be re-used for longer periods of time. If an affinity column is used first, it may become contaminated by pigments found in the crude cell extract and its capacity will generally decrease with use. Use in a first step of an anion exchange resin as described will allow the more expensive and difficult to prepare salicylate affinity column to be re-used repeatedly without loss of capacity.

Although samples may be added directly to the affinity or ion exchange column, it is preferred that any sample destined for either column be treated before its application to the column to remove ions and other low molecular weight species that may be present in the sample solution and which might adversely affect the properties of the column. Dialysis is a preferred method of sample treatment. When dialysis is used the solution against which the sample is being dialyzed (the dialysis solution) is preferred to be the solution that will be used initially to wash the column after the sample is applied thereto. The type of dialysis membrane is unimportant as long as the pore size is selected to retain proteins having a molecular weight of more than 10,000. Dialysis is normally carried out under conditions of refrigeration. The temperature should preferably be in the range from 2° to 8° C., with dialysis most preferably being carried out at about 4° C. The length of the dialysis period required varies with the relative volumes of sample and dialysis solutions and with the number of times the dialysis solution is changed, as is well known in the art. When the volume of dialysis solution is 5 times the volume of the sample, adequate removal of contaminating solution is obtained by overnight dialysis. Preferred is a 10:1 ratio of dialysis solution to sample with 20:1 being most preferred. With a 20:1 volume ratio, solute removal is sufficient after 6 hours. Preferred is dialysis for at least 12 hours, for example, overnight. When a 20:1 dialysis solution: sample ratio is used, the dialysis solution should preferably be changed once during an overnight dialysis. More frequent changing of the dialysis solution does no harm and speeds the removal of contaminating solutes. Dialysis against a continuous flow of dialyzer solution will work well but is not required. If continuous flow dialysis is not used, the dialysis solution should be circulated for better transfer of contaminating solutes away from the dialysis membrane. Stirring, for example with a magnetic stirrer, is one way of causing this circulation.

Once salicylate hydroxylase has been purified as described above or by any other procedure that removes measurable activity of other enzymes, the enzyme is suitable for use in clinical situations as an assay reagent for salicylate levels in body fluids. Examples of body fluids that may be tested for the presence or quantity of salicylate include plasma, serum, saliva, urine, gastric aspirate, tears, cerebrospinal fluid, and whole blood. The fluid chosen depends on the reason for performing the analysis. Routine monitoring in salicylate therapy is preferably done on serum or plasma. Emergency room analysis of potential toxic overdose cases may prefer saliva, urine, or gastric aspirate. Whole blood may be used (with at least one monitoring technique) when the sample that can be obtained is small, such as with infants. The test is intended primarily for use with humans although it may be used for other mammals that come into contact with salicylate, for example, domestic animals and household pets.

Pseudomonas salicylate hydroxylase quantitatively converts salicylate to catechol in the presence of NADPH/NADH and molecular oxygen as shown below:

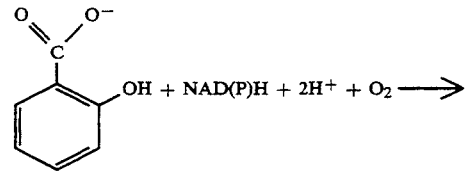

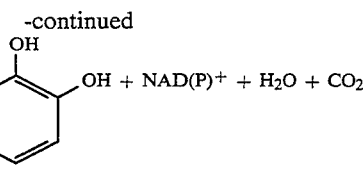

The amounts of reagents used are not critical, as long as salicylate remains the limiting reagent, and can be adjusted from the ranges given below as becomes necessary or for convenience. In order to provide a complete discussion, a total reaction mixture volume of one milliliter will be assumed for the present discussion. Proportional changes of the various volumes and amounts of reagents allow easy adjustment to any desired volume.

Generally the reaction is carried out in a buffered solution (unless pH change or $CO_2$ evolution is being measured). The buffer should offer near physiological conditions of pH and ionic strength for the enzyme. A potassium phosphate buffer, pH 7.6, at a concentration of 20 mM is preferred, although any pH from 6.5 to 8.9 and concentration from 5 to 100 mM is adequate. The sample may be added in any amount sufficient to trigger enzyme activity (if the salicylate is present in the sample) and the choice of sample size is discussed fully at a later time. From 1 to 40 $\mu$l per ml of total volume is convenient. Since the enzyme is generally available as a solution, it is conveniently added as such. About 10 $\mu$l of an enzyme solution containing 0.01 to 1 IU/ml is sufficient for most conditions, although the amount may be increased to speed up the reaction or decreased to slow the reaction down as needed. One IU (International Unit) is the amount of enzyme required to catalyze the disappearance of one $\mu$mole of NADH/min. NADH (or NADPH) may be present in a concentration of from about 10 to about 290 $\mu$M. Since the concentration of $O_2$ in aqueous media is between 0.20 mM and 0.30 mM, it is not necessary to keep NAD(P)H concentration higher than 0.30 nM. In cases where the reaction is monitored at 340 nm, NADPH is preferred to NADH (the enzyme shows the same Vmax toward NADH and NADPH) because occasionally both lactate dehydrogenase and pyruvate are found in human serum; if NADH is used, the concurrent presence of these two entities will cause an absorbance change at 340 nm, thus resulting in a false-positive reaction.

The progress of this reaction can be conveniently monitored spectrophotometrically, fluorometrically, or polarographically or any other method that will detect the chemical changes that occur, such as the dry reagent technique. Some other techniques are measurement of $CO_2$ formation (using a blood-gas analyzer or $CO_2$ electrode) and measurement of pH changes. Since all these methods possess the same high speed as an enzyme catalyzed reaction, they are perfectly suited for emergency identification and quantitation of salicylate as well as for routine therapeutic monitoring.

The salicylate hydroxylase reaction can be monitored spectrophotometrically either at a salicylate specific wavelength of about 300 nm or at a NADH/NADPH specific wavelength of about 340 nm. The absorbance maximum of salicylate occurs at 296 nm. However, 300 nm is better suited for samples containing serum because serum proteins in the reaction mixture show much lower background absorbance at this wavelength than at 296 nm, and the absorbance of salicylate at 300 nm is about 95% of the value at 296 nm. Grossly hemolyzed or icteric samples do not impair the monitoring at either 300 nm or at 340 nm.

By employing the double-beam mode in a spectrophotometer, any background absorbances (caused by, for example, turbid samples) will cancel each other in the two samples and a straight base line will be obtained at zero (or near zero) absorbance level. Since the absorbance of the mixture containing the enzyme decreases while that in the reference compartment remains unchanged, it is necessary to reverse the polarity of the recorder. If the polarity of a given recorder cannot be reversed, the enzyme can simply be added to the cuvette in the reference compartment.

The change of absorbance ceases when all the salicylate in the reaction mixture is consumed when salicylate is the limiting reagent. The time required for the completion of the reaction can be controlled by the amount of enzyme added; addition of 10 times more enzyme will result in the completion of the reaction in one-tenth the time.

The relationship between the absorbance change at 300 nm and serum salicylate level is linear as long as the sample does not cause the salicylate concentration in the reaction mixture to reach higher than 0.20 nM; above this concentration, the reaction may be stopped not by salicylate exhaustion but by oxygen depletion.

From a series of absorbance determinations, it was found that the conversion of one mg/ml salicylate to catechol accompanies an effective absorbance change (which includes the contribution from NADPH) of 37.63 at 300 nm in 20 mM KPi, pH 7.6. This value is equivalent to a millimolar effective extinction coefficient of 5.16 (cf. $E^{340}NADPH=6.22$, effective $E296$ salicylate$=4.70$). Although the salicylate level in the reaction mixture can be determined from the absorbance change observed and above extinction coefficient, it is more practical and accurate to calculate it by comparing the absorbance change caused by the sample with that caused by standards that contain known quantities of salicylate.

A salicylate concentration as low as 0.40 mg/dl and as high as 90 mg/dl can be quantitated by this method by using 0.03 ml of sample. The low limit is an order of magnitude lower than the low limit of the therapeutic range and normally this is well beyond the limit of clinician's interest. If a 0.03 ml serum sample from a patient causes an absorbance change of more than 1.00 (i.e. a sample with salicylate concentration higher than about 90 mg/dl), less serum can be added or it may be diluted until absorbance change falls below 1.00. If the salicylate level in serum is very low, it is possible to use more than 0.03 ml of sample. However, if the serum concentration reaches higher than 7% of the reaction mixture (v/v) the reaction rate slows down considerably.

There is a weak blank reaction with salicylate hydroxylase (i.e. absorbance change taking place in the absence of added salicylate). This reaction, which can be noticed only when a spectrophotometer is expanded to its maximum sensitivity scale, is caused by the enzyme-bound salicylate (the enzyme was exposed to salicylate during purification). Although it is known that salicylate hydroxylase exhibits an NADPH oxidase activity at the extent of 0.43% of the hydroxylase activity, this oxidase activity is not apparent under normal reaction condition. The oxidase activity is apparent if the absorbance continuously and steadily changes in the absence of salicylate.

Some spectrophotometers have only single beam capacity. Also, there are many models of spectrophotometer which are not equipped with a U.V. source (e.g. Gilford Stasar III), making absorbance measurement at 300 nm impossible. The present enzymatic method has no difficulty with these kinds of spectrophotometers, since monitoring can also be carried out at 340 nm (Tungsten lamp) employing NADH and the-single beam mode. A serum sample containing as low as 1.57 mg/dl salicylate causes a significant decrease in absorbance at 340 nm. However, upon addition of the enzyme, NADH is slowly and continuously oxidized even in the absence of salicylate. This blank reaction, which is not apparent when NADPH is used, is caused by the enzyme's NADH oxidase activity. The enzyme has an NADH oxidase activity at the extent of 2-4% of its hydroxylase activity. The NADH oxidase activity is, however, so weak that, for all practical purposes, it does not interfere with salicylate quantification.

There is also a linear relationship between the absorbance change at 340 nm and the sample salicylate concentration. In this case, the results obtained with 0.03 ml samples having salicylate concentrations of 70 mg/dl (which give a salicylate contration of 0.20 mM in the reaction mixture) or higher deviate from linearity because of $O_2$ exhaustion.

The results obtained by monitoring the reactions at 300 nm correlate with those obtained by monitoring at 340 nm. Because the effective extinction coefficient of salicylate at 300 nm is smaller than the extinction coefficient of NADH at 340 nm by a factor of 0.83, at a given salicylate concentration, the absorbance change at the former is smaller than that at the latter. When the absorbance changes obtained at 340 nm are multiplied by 0.83, the resulting values overlap with the experimentally observed absorbance changes at 300 nm. It should be pointed out that the absorbance ratio of 0.83 (the rule of 0.83) is specific for salicylate and can be used as a test for interfering reactions; reactions involving compounds other than salicylate give different ratios. Generally speaking, however, the other salicylate enzyme substrates that might cause an interfering reaction are rarely encountered in a clinical situation.

The results of both monitoring cases (i.e. at 300 nm and 340 nm) deviate from linearity when the reaction mixtures have salicylate concentrations higher than 0.20 mM. In addition, when NADH is used, it is possible to get false-positive react ions if pyruvate and lactate dehydrogenase are concurrently present in the sample.

It is known that the enzyme can oxidize NADH/NADPH in the presence of benzoate (a pseudosubstrate or uncoupler). However, the react ion involving benzoate can be immediately distinguished from that involving salicylate because the rate of the former is much slower than that of the latter. Thus, under the present assay condition for a 1 ml total volume the reaction involving benzoate takes much longer than the normal 1-3 minutes to reach the end point. Although the enzyme shows the same $V_{max}$ toward benzoate and salicylate, its $K_m$ for benzoate (2,000 μM) is about three orders of magnitude larger than that for salicylate (2.7 μM). Thus, under the present assay system, it takes 0.03 ml of serum sample having a benzoate concentration of 834 mg/dl (which will give a $K_m$ concentration) in order to reach a rate of half Vmax. Therefore, in the case of the reaction involving benzoate, it is not necessary to apply the rule of 0.83 to determine if the reaction is being caused by salicylate or another component of the test fluid.

Salicylate hydroxylase is a remarkably stable enzyme. Neither storing the purified enzyme at 4° C. for three weeks nor repeated freezing and thawing causes loss of its activity; the activity remained within ±10% of the original activity throughout. The unpurified enzyme, however, will lose considerable activity upon storing at 4° C., probably due to the action of some proteases in the crude extract.

Anti-coagulating agents such as EDTA, oxalate and citrate do not inhibit the enzyme; heparin was also found to have no effect on it. Therefore, both serum and plasma can serve as samples for the analysis. Phenothizaines and acetaminophen do not interfere with the enzyme activity. White-Stevens and Kamin found that there was no product inhibition either by NAD(P)+, the oxidized forms of NADH and NADPH, or by catechol. Body fluids other than serum (e.g. saliva, urine, CSF) are all acceptable as samples; in fact, because of low protein contents, these fluids are even better samples than serum/plasma.

This enzymatic method is superior to any of the currently available methods for salicylate analysis for the following reasons:

a) It is very quick and the speed of the analysis can be controlled by the amount of enzyme added; if desired, the reaction can be completed within less than 5 seconds. No current method is as nearly fast as this method (the Trinder method takes a minimum of 10 minutes if the centrifugation step is required).

b) It requires only a spectrophotometer—a instrument in most, if not all, toxicology and clinical chemistry laboratories. Most technicians can operate this instrument as a basic skill. GC and LC require expensive instruments and highly trained specialists. In addition, these chromatographic methods are very costly because they require a constant supply of gas or elution reagents of extremely high purity.

c) It does not require sample preparation steps such as extraction, deproteinization or centrifugation. It uses neither corrosive reagents nor heavy metals (Hg, W, and Fe are potential environmental pollutants).

d) It takes only 0.03 ml or less sample to detect a sample salicylate level of 0.4 mg/dl. It is, therefore, especially advantageous in case a sample has to be obtained from an infant.

e) It is very specific for salicylate. In suspicious cases, however, the application of the "rule of 0.83" or an examination of the reaction rate can prove if the reaction involves salicylate. No drug or physiological metabolite has been found to interfere with this method.

The most useful application of this enzymatic method is adopting it to commercial auto analyzers (e.g. CentrifiChem, ABA-100, aca, Beckman TR, RotorChem, Gemsaec, SMAC, etc). The procedures for the adoption depend on the requirements and capacities of individual analyzer and can easily be determined by routine experimentation.

Under certain circumstances (e.g., pathology examinations) it may be absolutely necessary to detect and quantitate a trace of salicylate. An extremely high sensitivity can be achieved if the disappearance of reactants (i.e. salicylate and NADPH/NADH) are measured fluorometrically. Salicylate can be specifically monitored by exciting at 305 nm and measuring the fluorescence emission at 400 nm; likewise, the disappearance of NADPH/NADH can be monitored by exciting at 340–365 nm and measuring emission at 440–480 nm. The excitation emission wavelength pair for salicylate does not overlap with that for NADPH/NADH.

Since most fluorometers can measure an NADPH/NADH concentration as low as $10^{-10}$ M, it is expected that this fluorometric method is able to detect a pg range of salicylate in the reaction mixture. In general, the same reagent mixture can be used as described above for spectrophotometry. In this method the NADPH/NADH concentration, however, must be kept far lower than that used in the spectrophotometric method; high concentrations of NADPH/NADH result in strong fluorescence, which masks small changes (caused by low salicylate concentrations) in fluorescence.

Because the salicylate hydroxylase reaction consumes oxygen stoichiometrically, salicylate can also be quantitated by measuring the change of oxygen concentration in the reaction medium with a Clark electrode. Once again, the previously described reaction mixture can be used.

A reaction mixture composed of 20 mM KPi, 0.29 mM NADPH/NADH, pH 7.6, and a 0.03 ml clinical sample (or a standard, which has a known quantity of salicylate) in a total volume of 1.80 ml (the capacity of most Clark electrode cells) is placed in the cell, in one typical set-up. The reaction is then initiated by the addition of the enzyme. The quantity of salicylate is determined by comparing the amount of oxygen consumed in the presence of a clinical sample and that consumed in the presence of standards. Here again, the concentration of salicylate in the reaction mixture should not exceed that of the dissolved $O_2$. Therefore, the point of $O_2$ exhaustion should be pre-determined by adding a few grains of dithionite.

This polarographic method is by far the simplest and least expensive method. Because no light is involved in monitoring $O_2$ tension by a Clark electrode, the reaction mixture does not have to be optically clear. Salicylate can be analyzed by adding whole blood (blood cells do not respire) into the electrode chamber. This method, therefore, eliminates the step of serum preparation.

A recent development in the area of clinical analytical testing is the dry reagent technique. A strip of filter paper, or a similar solid dry support, non-reactive substrate, is impregnated with all of the reagents except the sample to be analyzed and dried. Addition of the sample provides the fluid medium in which the reaction may take place. The reaction is monitored by measuring the change in light reflected from the sample spot using a spectrophotometer capable of measuring reflected light. This method is very convenient (no mixing is required) and allows the use of very small samples.

The reagents required for the above described analytical procedures may be made available in kit form. Such a kit would minimally contain the salicylate hydroxylase in a form suitable for use in the type of test procedure being used. This could be in solution, or the enzyme could be present in lyophilized form, ready for activation by addition of a suitable buffer, or in low temperature ($< -20°$ C.) ethylene glycol. The buffer could contain NADH or NADPH, or a separate solution of these reagents could be provided. Either the buffer or NAD(P)H could be present in dry form, ready for addition of a measured quantity of distilled or deionized water for reconstitution. If the dry reagent technique is to be used, all the reagents could be present impregnated into a piece of filter paper or other suitable substrate. Standard salicylate solutions of known concentration may also be present in the test kit.

The above disclosure generally describes the present invention. A more complete understanding can be obtained by reference to the following specific examples, which are provided herein for purposes of illustration only and are not intended to be limiting unless otherwise specified.

EXAMPLE 1

Purification of Salicylate Hydroxlase

Growth of organism. A lyophilized form of Pseudomonas sp. RPP (ATCC 29351) was purchased from the American Type Culture Collection and revived in the liquid medium containing 1% Difco yeast extract according to the instruction that accompanied the culture.

A loopful of the medium containing the revived cells was transferred into 50 ml of the salicylate sole-carbon source medium, which was described by White-Stevens and Kamin in J. Biol. Chem. (see above) for the optimal induction of salicylate hydroxlase. After 2 days of growth with vigoruous shaking at 37° C., the yellowish culture was transferred into a flask which contained 12 liters of the same medium, and the culture was continued for 1 more day, at which time the organism was innoculated into a 200-liter capacity fermentor. The growth conditions were in general the same as those described by White-Stevens and Kamin except that no attempt was made to control the pH and salicylate concentration of the medium during the growth since no attempt was made to optimize the yield of enzyme. When the $A_{600}$ of the medium reached 1.7 approximately 19 h after the innoculation, the cells were harvested with a Sharples centrifuge. The yield from this fermentation was 420g(wet wt).

Coupling of p-aminosalicylate to the activated CH-SEPHAROSE 4B (beaded agarose). Approximately 12 g (dry wt) of the activated CH-SEPHAROSE 4B from Pharmacia Fine Chemicals were washed with 2.4 liters of 0,001 N HCl in a sintered glass filter. The washed beads were mixed with 360 ml of 100 mN $NaHCO_3$ solution which also contained p-aminosalicylate and NaCl at the concentrations of 40 and 400 mM, respectively. The mixture was then rotated, washed, treated with ethanolamine, and alternatively washed with the acidic and basic buffers according to the instruction that accompanied the beads.

Preparation of crude extract. Chilled 20 mM potassium phosphate buffer, pH 7.6, was added to the bacterial paste at the ratio of 6.6 ml/g (wet wt) bacteria. The resulting suspension was mechanically stirred at 4° C. until it became clump free and then sonicated with a W-375 sonicator (Heat System) for 2 min with 1 min pausing for cooling at half-minute sonication intervals. The sonicated material was then centrifuged for 30 min at 30,000 rpm (No. 30 rotor) in a Beckman L5-50 centrifuge to remove insoluble debris. The resulting clear brownish crude extract was used for the subsequent chromatographic procedures.

Affinity chromatography with the salicylate column. In order to determine whether the salicylate column showed any affinity toward salicylate hydroxylase and, if it did, at what capacity, the crude extract was dialyzed overnight against 10 mM KPi, pH 7.6, and loaded on a column which was packed with the salicylate-coupled beads (1.9×8.0 cm) and equilibrated with the above dialysis buffer.

After the loaded column was washed with approximately 10 column volumes of the same buffer, a linear gradient system consisting of 100 ml of 10 mM potassium phosphate, pH 7.6, and the same volume of the same buffer which also contained.60 mM sodium salicylate was applied to it. The effluents from the wash and gradient elution were then assayed for enzyme activity. The flow rage was 0.7 ml/min and the fraction size was 5.5 ml.

Used salicylate columns were routinely recycled by washing them with 50 ml of a solution containing urea and NaCl at concentrations of 6 and 1 M, respectively, followed by reequilibration with 100 ml of 10 mM potassium phosphate, pH 7.6.

Enzyme Assay. The assay procedure for the enzyme and the definition of the enzyme were the same as that described in White-Stevens and Kamin (1970) except that EDTA and FAD were excluded in the assay mixture of the present work. The extinction coefficient of $6.22 \times 10^3$ $M^{-1}cm^{-1}$ was used to convert the $A_{340}$ change to micromoles of NADH oxidized.

General Purification Procedure. When the usefulness of the salicylate column was proven, the following purification steps were adopted. After the crude extract was dialyzed overnight against 20 mM potassium phosphate, pH 8.5, it was loaded on a DE-52 column, which had been equilibrated with the same buffer. The size of the column varied depending on the amount of protein present in the crude extract; routinely, 13 mg of protein was loaded per 1 ml of the packed anion-exchanger in a column of 1.9 cm diameter.

The column was then washed with several column volumes of the same pH 8.5 buffer followed by elution with a potassium phosphate gradient system, consisting of 1 liter of 20 mM $K_2HPO_4$, pH 8.5, and the same volume of 200 mM $K_2HPO_4$, pH 8.5. The flow rate of this elution was 0.9 ml/min and the fraction size was 8.5 ml.

The enzymatically active fractions were pooled, dialyzed against 10 mM potassium phosphate, pH 7.6, and a volume of the dialyzed protein solution containing 95±10 units of the enzyme was loaded on the salicylate affinity column and chromatographed according to the procedure presented in the pertinent section above.

Figure 2:
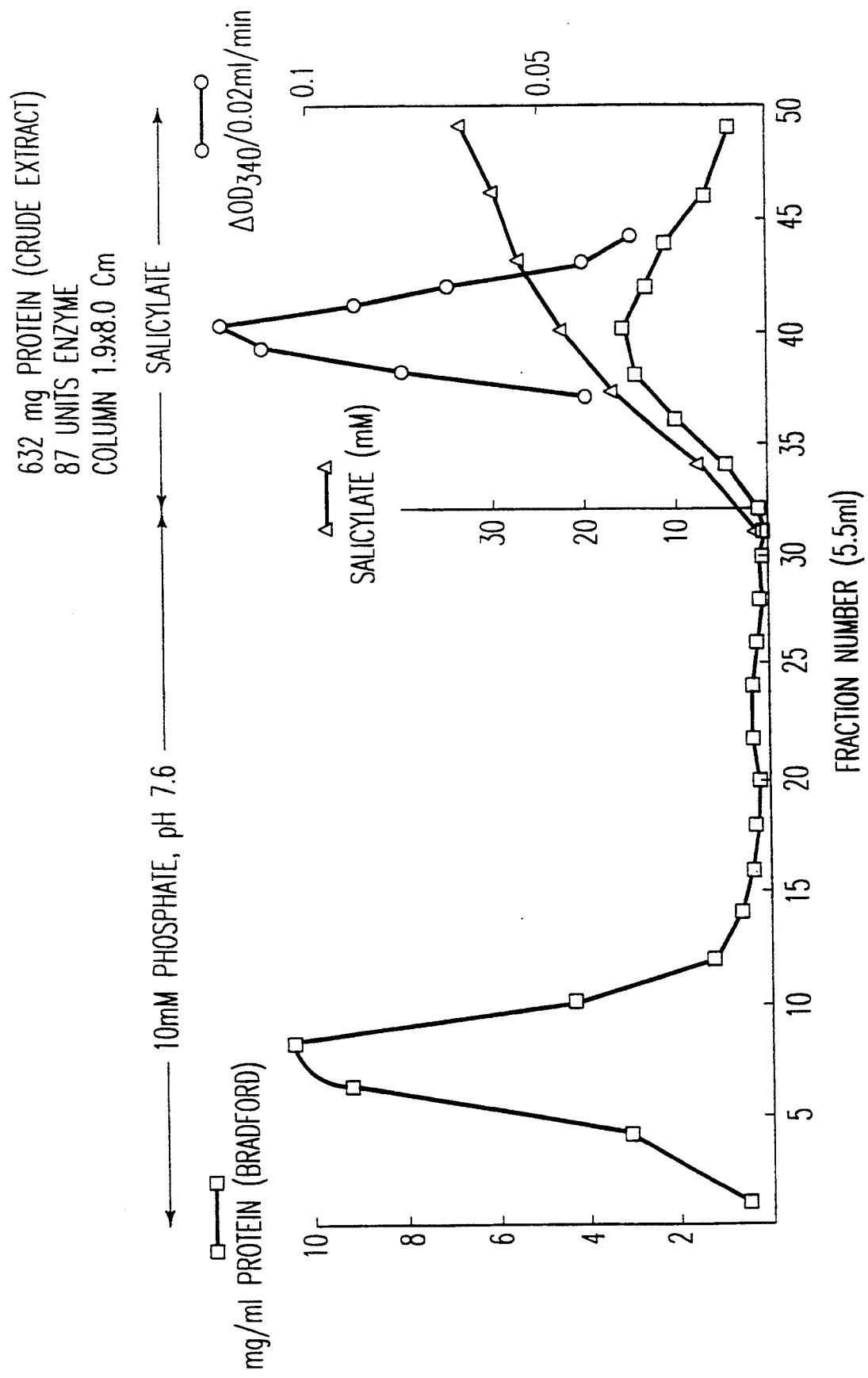
FIG. 2 shows purification of salicylate hydroxylase on a salicylate affinity column.

FIG. 2 shows the elution profile of protein and salicylate hydroxylase during the chromatography of the bacterial crude extract through the salicylate column. A bulk of turbid brownish materials, which were devoid of the enzyme activity, emerged from the column during the loading and also when the crude extract-loaded column was washed with 20 mM potassium phosphate, pH 7.6, while a bright yellow material accumulated and was visible near the top of the column.

During the gradient elution of the affinity column, this yellow material moved through the gel and eluted concomitantly with the enzyme activity, reaching its highest level when the salicylate concentration approached 25 mM (FIG. 2). The specific activity of the enzyme in the affinity effluent was increased eight-fold compared with the crude extract. The maximum capacity of the column was found to be 6 units of the enzyme per 1 ml of the packed beads.

This salicylate column was very stable. It has been recycled several dozen times over a period of 8 months without detectable loss of its specificity or capacity.

The same degree of purification was achieved whether the crude extract was chromatographed first with the anion exchanger followed by the affinity step or vice versa. However, the former is definitely preferred to the latter; if the unfractionated crude extract was directly loaded on the affinity column, a dark greenish component(s), which stubbornly stuck to the column and could not be removed by the recycling procedure, caused a gradual loss of the column's capacity.

Table 1 summarizes the specific activity and yield of the enzyme during the course of the purification. It shows that the nearly pure enzyme has a specific activity of 14.9 units/rag and that the overall recovery is 62%.

TABLE 1

PURIFICATION OF SALICYLATE HYDROXYLASE

| step | Volume (ml) | Protein concentration (mg/ml) | Total protein (mg) | Specific activity (units/mg) | Total activity (units) | Yield (%) | Purification (n- fold) |
|---|---|---|---|---|---|---|---|
| Crude extract | 102.7 | 5.0 | 513.5 | 0.3 | 154 | 1.0 | 1.0 |
| DE-52 | 25.9 | 1.4 | 36.3 | 2.9 | 105 | 68 | 9.6 |
| Salicylate affinity | 15.9 | 0.4 | 6.4 | 14.9 | 95 | 62 | 50.0 | bance changes caused by low levels of salicylate. Again, the reaction shows linear changes with salicylate concentration up to the point where oxygen depletion comes into effect.

The spectrophotometrically-measured (340 nm) enzyme reaction has been tested both for precision and for correlation with the results of the Trinder test. Table 2 shows the precision (both within-run and between-run) for various concentrations of salicylate samples in serum. The serum concentrations were not set at a particular value prior to analysis.

TABLE 2

| PRECISION OF ENZYMATIC METHODS | | | |
|---|---|---|---|
| $\overline{x}$ mg/dl | n | SD mg/dl | CV % |
| Within-run | | | |
| 3.06 | 9 | 0.10 | 3.27 |
| 11.84 | 12 | 0.43 | 3.63 |
| 21.76 | 11 | 0.85 | 3.91 |
| 32.59 | 12 | 1.07 | 3.28 |
| 50.32 | 9 | 1.29 | 2.56 |
| Between-run | | | |
| 12.50 | 8 | 0.55 | 4.40 |
| 22.28 | 8 | 0.80 | 3.59 |
| 31.88 | 8 | 0.63 | 1.98 |
| 48.78 | 8 | 0.70 | 1.44 |

EXAMPLE 2

Figures 3A, 3B, 3C:
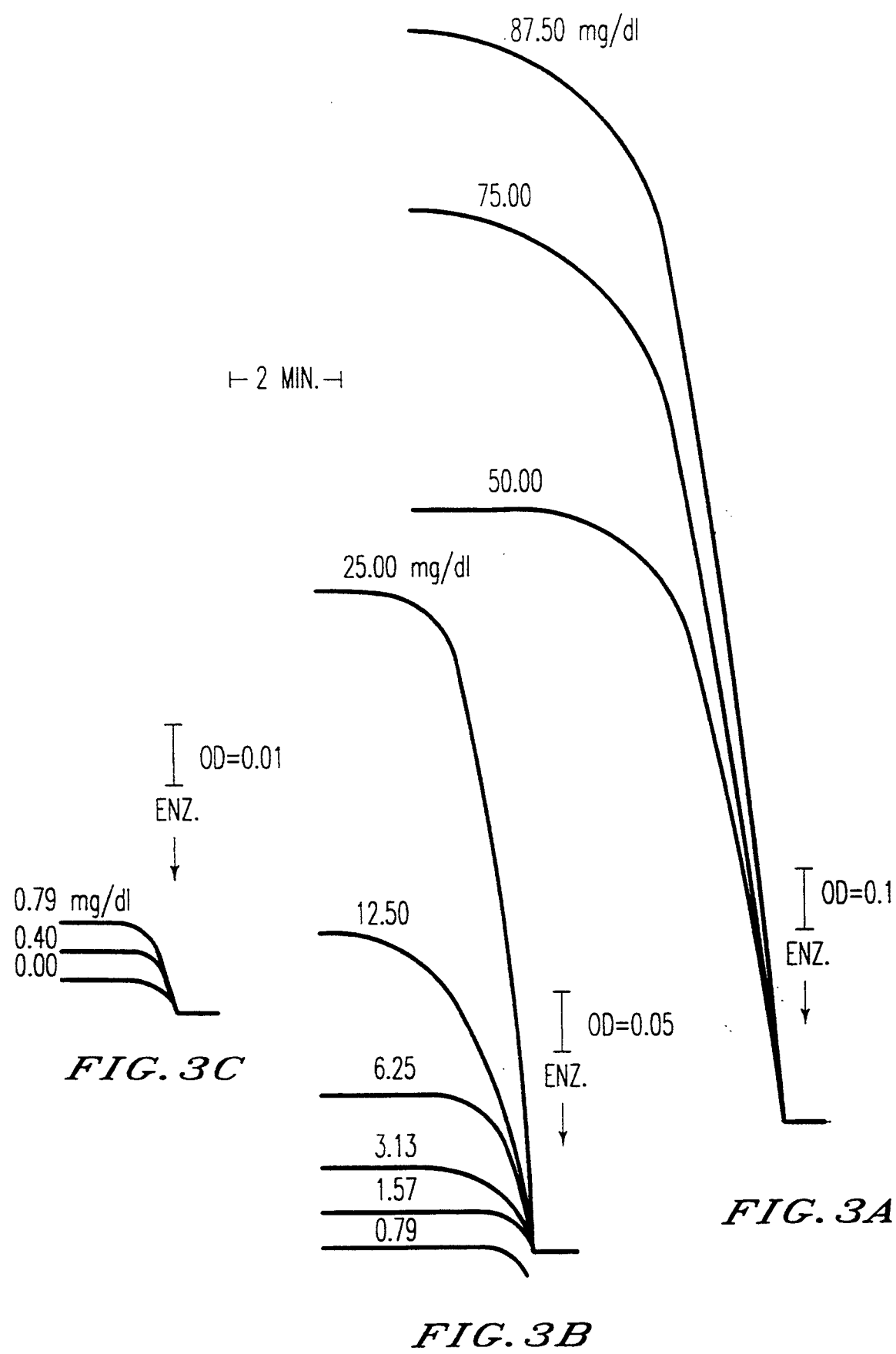
FIGS. 3A, 3B and 3C show quantitation of salicylate in serum by an enzymatic method using salicylate hydroxylase in which the disappearance of salicylate is measured.
Figure 4:
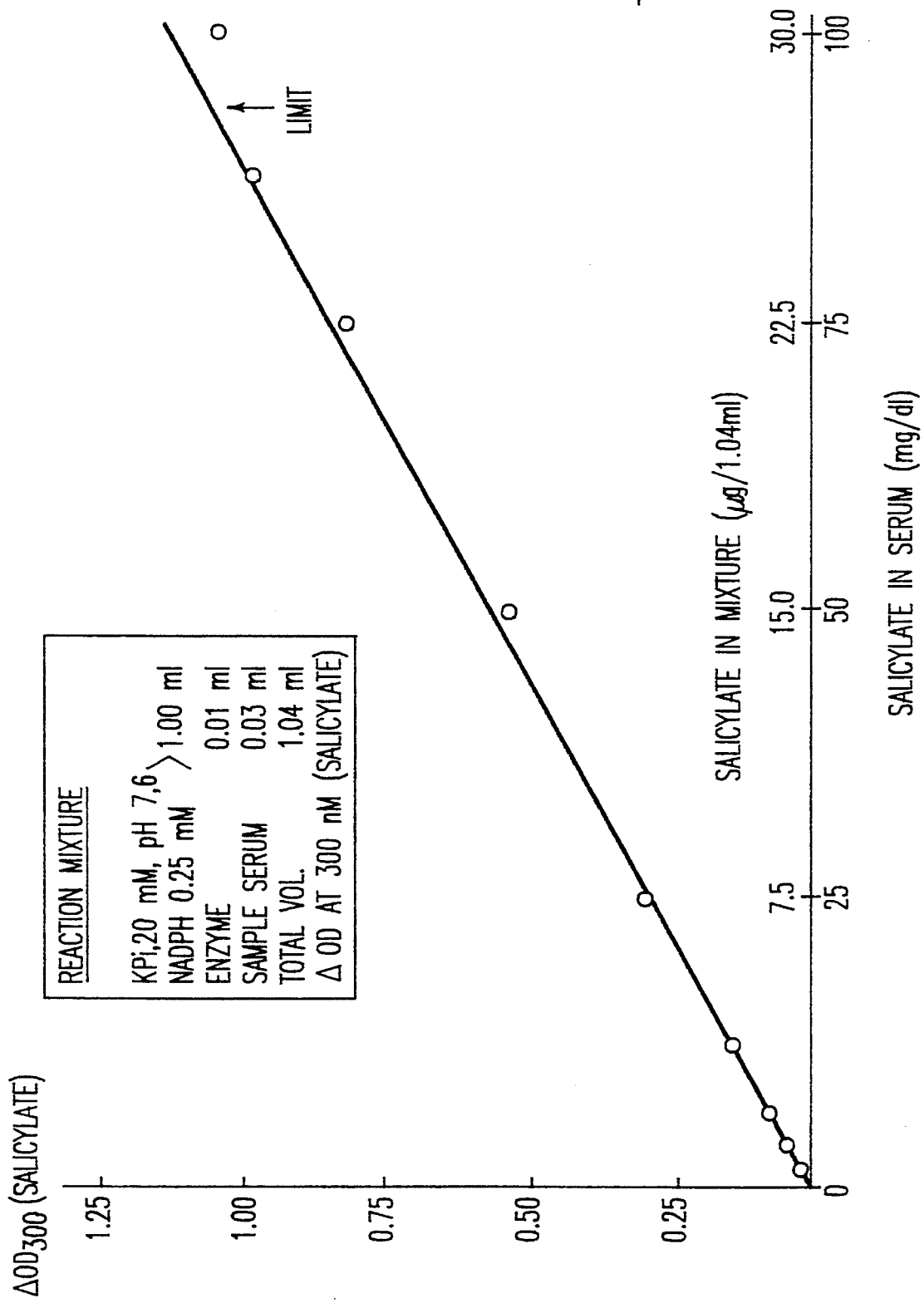
FIG. 4 shows the linearity of the data disclosed in FIG. 3.

Use of Salicylate Hydroxylase in Spectrophotometric Analysis of Salicylate Levels in Serum and Plasma For these experiments, two cuvettes containing identical reaction mixtures composed of 1.00 ml of 20 mM KPi - 0.25 mM NADPH, pH 7.6, and 0.03 ml of serum sample were prepared. One cuvette was placed in the reference compartment and the other in the sample compartment of a double-beam spectrophotometer. Salicylate hydroxylase (0.01 ml) was then added into the cuvette in the sample compartment and the absorbance change was recorded. (The enzyme was first loaded on a small glass loop, which was quickly inserted into the react in mixture and shaken). FIG. 3 shows actual spectrophotometer tracings of the absorbance changes at 300 nm. These changes are linear up to a salicylate concentration of 0.20 mM in the reaction cuvette (FIG. 4). At higher concentrations the non-linearity is caused by oxygen depletion. This is the reason why the result obtained with the sample containing 100 mg/dl salicylate (0.03 ml of which result in a salicylate concentration of 0.21 mM under the present assay condition) in FIG. 3 deviates from the linearity. (Under the present conditions, where the total volume of the reaction mixture is 1.04 ml, a 0.03 ml sample having a salicylate concentration of 95.1 mg/dl gives a final salicylate concentration of 0.20 mM.

Figure 5:
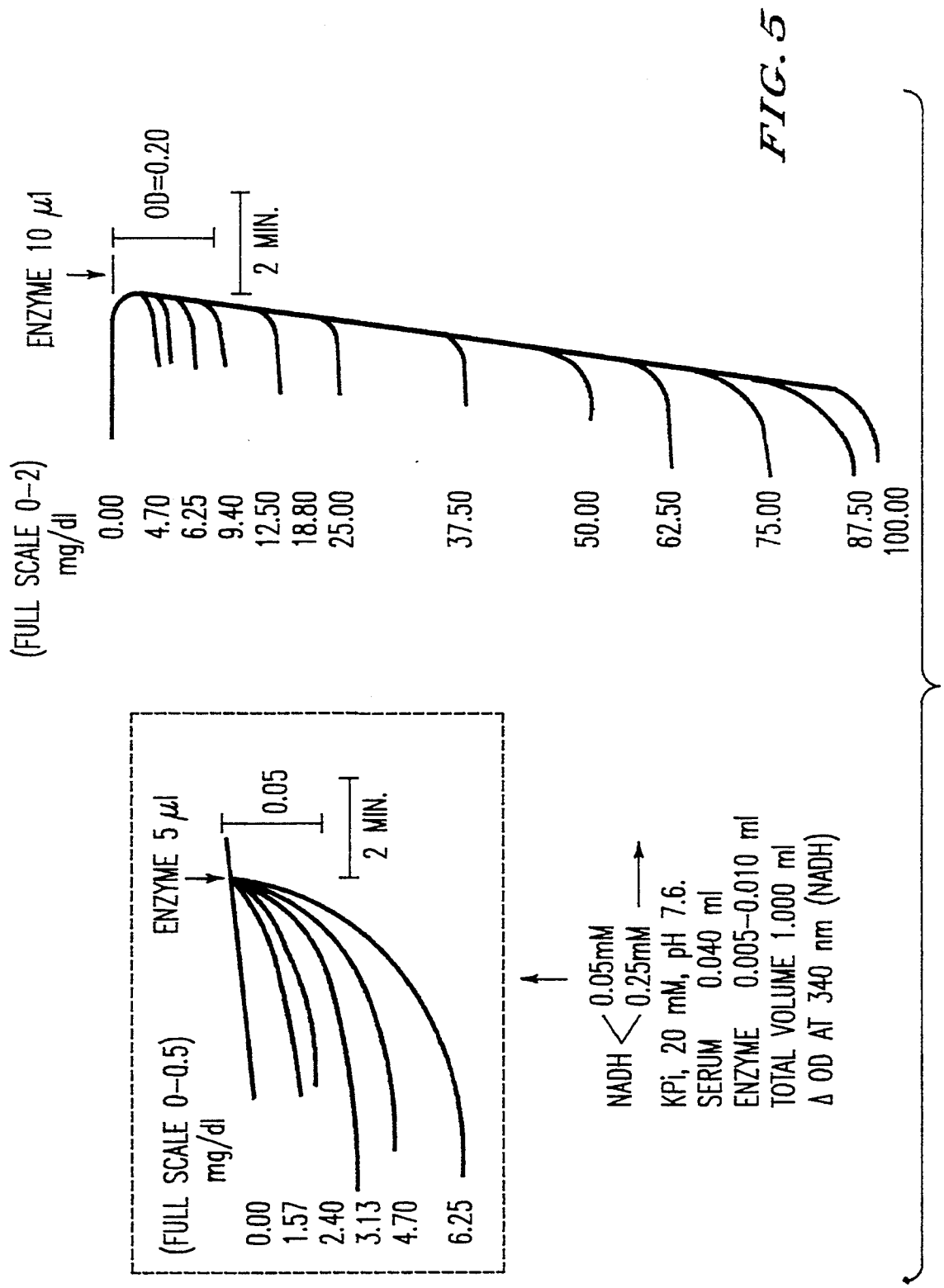
FIG. 5 shows quantitation of salicylate in serum by an enzymatic method using salicylate hydroxylase in which the disappearance of NADH is measured.

FIGS. 4 and 5 show the results of similar experiments carried out at 340 nm (Tungsten lamp) employing NADH and a single beam spectrophotometer. A cuvette containing 1.00 ml of reaction mixture composed of 20 mM KPl, pH 7.6, 0.25 mM (or 0.05 mM when salicylate concentrations were low) NADH, 0.040 ml of serum sample, and 0.005–0.010 ml of enzyme was placed in the instrument. The full recorder scale was 0-2 absorbance unit when NADH concentration was 0.25 mM; however, in the case of 0.05 mM NADH (insets of FIGS. 5 and 6) the full recorder scale was expanded to 0 0.05 absorbance unit in order to detect small absor- As can be seen the coefficient of variance (CV) is well within acceptable standards.

Figure 8:
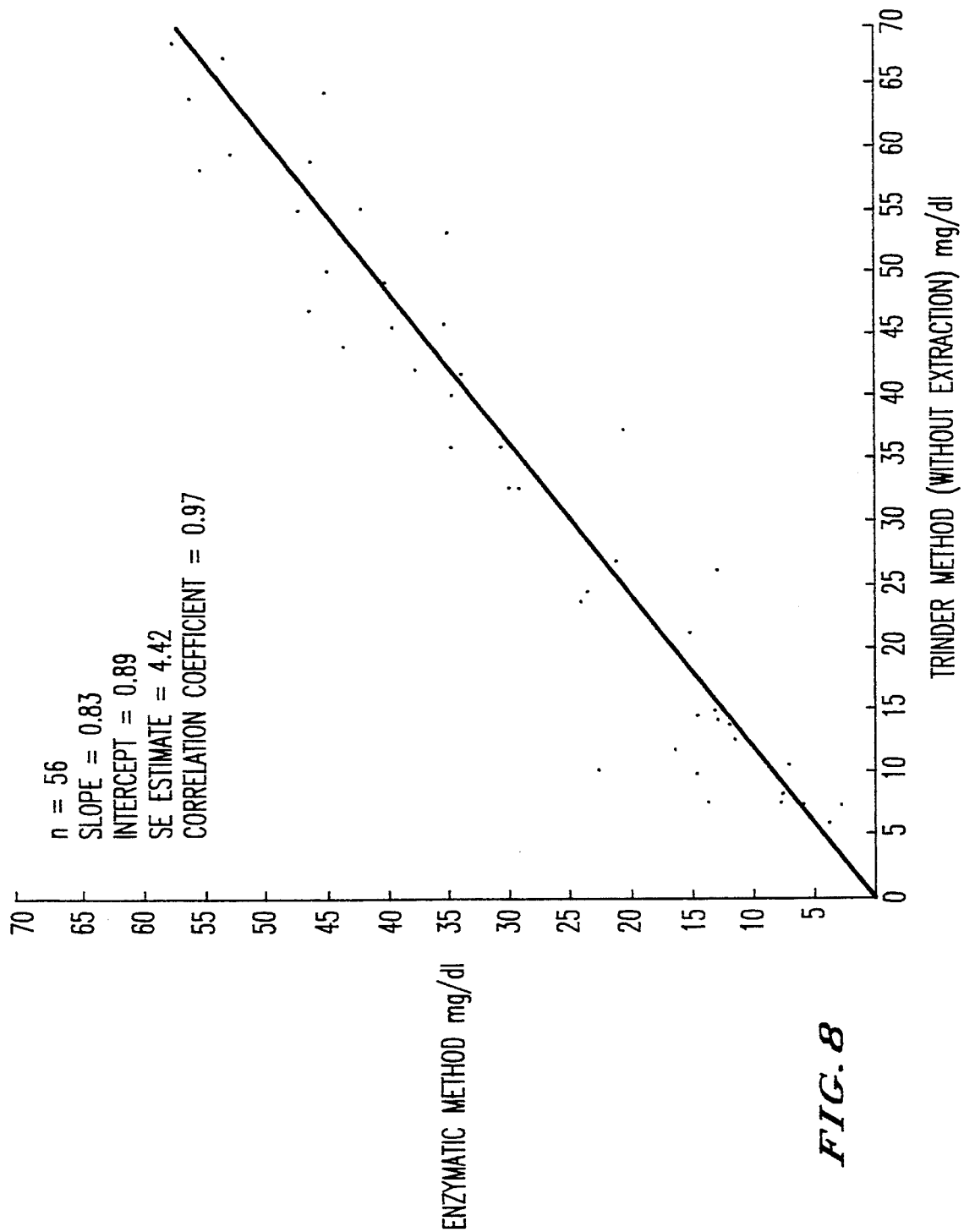
FIG. 8 shows the correlation between results obtained by the manual spectrophotometric enzymatic method and the Trinder test.

FIG. 8 shows the correlation between the results obtained by the enzymatic method and by the Trinder method. Excellent correlation was found, as demonstrated by the correlation coefficient of 0.97.

EXAMPLE 3

Storage Stability of Salicylate Hydroxylase. Salicylate hydroxylase enzyme was isolated from Pseudomonas sp. RPP by the techniques described above and its stability to storage was determined at various stages of purification. The results are shown in FIG. 7. The enzyme purified according to the above-described general procedure did not lose any of its activity either when stored at 4° C. for three weeks or when subjected to seven cycles of freezing and thawing. Activity remained within ±10% of the original activity throughout for either process (except for an apparent spurious high value after the sixth freeze-thaw cycle). The unpurified enzyme in the crude cell extract lost considerable activity, particularly when stored at 4° C., probably because of protease activity present in the extract. In all cases, the enzyme was stored in the solution in which its was normally found at that stage of purification.

EXAMPLE 4

Application of Salicylate Hydroxylase to Salicylate Analysis in an Automatic Analyzer The analytical procedure has been adapted by the present inventor to the CentrifiChem System 500 automatic centrifugal analyzer. Using the instrument settings set forth below, the results obtained by this method agree excellently with the conventional Trinder test. The instrument settings given here are not intended to represent the only settings that will work or to be otherwise limiting, but are an example of settings that will provide accurate and reproducible test results.

Instrument Settings

I. Pipettor (CentrifiChem System 500)
a. sample volume - 2- 1
b. sample +diluent volume - 50 1 (diluent is 20 mM kPi, pH 7.6)
c. reagent 1 - 50 1 (reagent is NAD(P)H in 20 mM kPi, pH 7.6 with an optical density at 340 nm of about 1.7)
d. reagent 2 - 50 1 (0.04 IU of salicylate hydroxylase)

II. Analyzer (CentrifiChem System 500)
a. To - 3 sec
b. T - 4 rain
c. abnormal absorbance - 2.0
d. blank - auto.
e. test mode - terminal
f. print-out - conc.
g. conc. factor/std. volume - 9.35
h. number of print - 1
i. test code - 00
j. temperature - 37° C.
k. filter - 340

III. Computer (parameters)
a. test name - Salicylate
b. test code - SAL
c. precision - 1
d. TO - 3 sec.
e. T- 240 sec
f. exhaust limit - 64.0 mg/dl
g. concentration - 0000
h. reaction type - 0
i. units - 0
j. standard 1 - 6.3 mg/dl
k. standard 2 - 12.5 mg.dl
l. standard 3 - 25.0 mg/dl.

Figure 9:
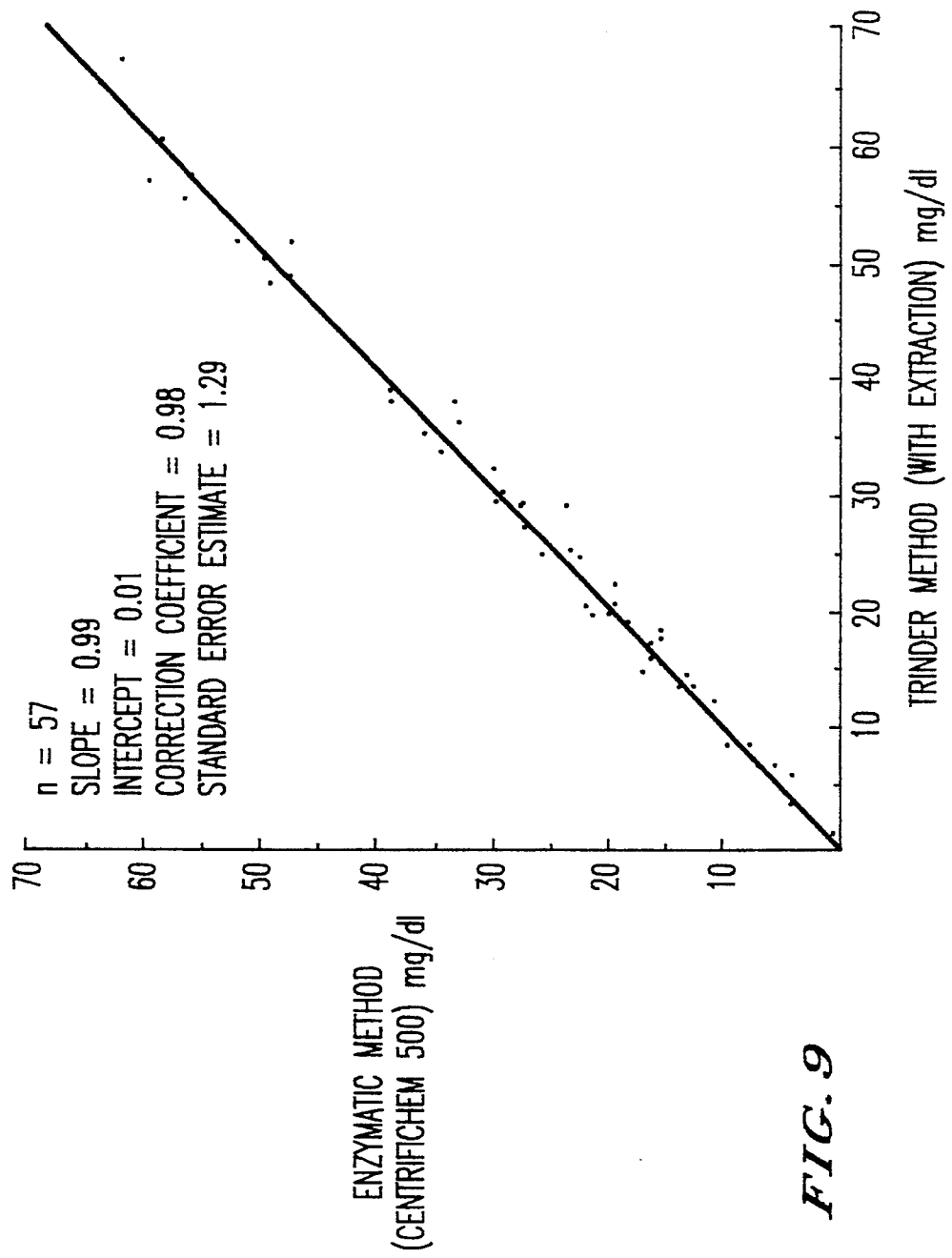
FIG. 9 shows the correlation between an automatic analyzer enzymatic method and the Trinder test.

FIG. 9 shows the correlation between the results of the CentrifiChem 500 (enzymatic) analysis and the Trinder method applied to identical serum samples containing salicylate. As can be seen from the correlation coefficient of 0.98, correlation is excellent.

Table 3 shows the precision of results obtained using the CentrifiChem 500 system. As with the manual spectrophotometric method, excellent precision is seen, as indicated by the coefficients of variance in the Table.

TABLE 3

PRECISION OF ENZYMATIC METHOD (Centrifichem 500)]

| x mg/dl | n | SD mg/dl | CV % |
|---|---|---|---|
| 6.4 | 10 | 0.14 | 2.2 |
| 16.5 | 10 | 0.82 | 5.0 |
| 24.95 | 10 | 0.35 | 1.40 |
| 37.8 | 10 | 0.42 | 1.1 |
| 47.4 | 10 | 0.54 | 1.1 |
| 54.3 | 10 | 0.39 | 0.7 |
| 60.8 | 10 | 0.56 | 0.9 |

The invention now being fully described, it will be apparent to one of ordinary skill in the art that many changes and modifications can be made thereto without departing from the spirit in scope of the invention as set forth herein.

What is claimed as new and desired to be secured by Letters Patent of the United States is:

1. A method for quantitating the amount of salicylate present in serum, plasma or whole blood containing salicylate, comprising:
   (i) reacting a non-deproteinized sample of the serum, plasma or whole blood containing salicylate with a Pseudomonas salicylate hydroxylase in the presence of $O_2$ and NAD(P)H until all the salicylate in said sample has been converted into catechol; and
   (ii) quantitate the amount of salicylate converted to catechol to determine the amount of salicylate in said sample.

2. The method of claim 1, wherein said hydroxylase has a concentration of 0.01-1 IU/ml and said NAD(P)H has a concentration of about 10 to about 290 $\mu$M during said reacting step.

3. The method of claim 1, wherein NADH is used in said reacting step.

4. The method of claim 1, wherein NADPH is used in said reacting step.

5. The method of claim 1, wherein said hydroxylase is salicylate 1-monooxygenase EC 1.14.13.1 isolated from Pseudomonas species RPP.

6. The method of claim 1, wherein said determining step is conducted spectrophotometrically, fluorometrically or polarographically.

7. The method of claim 1, wherein said serum, plasma or whole blood sample is a serum sample and wherein said determining step comprises measuring light absorbed by salicylate or NAD(P)H in said reacted sample at a wavelength of about 300 nm or at a wavelength of about 340 nm, respectively.

8. The method of claim 1, wherein said determining step comprises measuring the fluorescence emission of salicylate, NADPH or NADH in said reacted sample.

9. The method of claim 1, wherein said determining step comprises measuring the amount of NADPH or NADH oxidized in said sample.

10. The method of claim 1, wherein said salicylate hydroxylase is present on a solid support and said determining step comprises measuring the amount of light reflected from said solid support.

11. The method of claim 1, wherein said reacted determining step comprises measuring the amount of $O_2$ consumed by said sample by polarography.

12. A method for quantitating the amount of salicylate present in serum, plasma or whole blood containing salicylate, comprising the steps of:
   (i) reacting a non-deproteinized sample of the serum, plasma or whole blood containing salicylate with 0.01-1 IU/ml salicylate 1-monooxygenase EC 1.14.13.1 isolated from Pseudomonas species RPP in the presence of $O_2$ and about 10 to about 290 $\mu$M of NAD(P)H until all the salicylate in said sample has been converted into catechol; and
   (ii) quantitate the amount of salicylate converted to catechol to determine the amount of salicylate in said sample.

13. The method of claim 12, wherein said hydroxylase is reacted in the presence of $O_2$ about 10 to about 290 $\mu$M of NADPH.

14. The method of claim 13, wherein said sample is a serum or plasma sample.

15. The method of claim 13, wherein said sample is a whole blood sample.

* * * * *

UNITED STATES PATENT AND TRADEMARK OFFICE
CERTIFICATE OF CORRECTION

PATENT NO. : 5,362,630
DATED      : November 8, 1994
INVENTOR(S) : Kwan-sa YOU

It is certified that error appears in the above-indentified patent and that said Letters Patent is hereby corrected as shown below:

Title page, item [54], and col. 1, line 2, "HYDROXLASE" should read --HYDROXYLASE--.

Column 15, line 44, "0,001" should read --0.001--; and
               line 54, "mi/g" should read --ml/g--.

Column 16, line 8, "contained.60" should read --contained 60--; and
               line 12, "rage" should read --rate--.

Column 17, line 17, "units/rag" should read --units/mg--.

Column 19, line 26, "rain" should read --min--.

Column 20, line 41, "said sample." should read --said reacted sample.--.

Signed and Sealed this

First Day of April, 1997

BRUCE LEHMAN

Attest:

Attesting Officer

Commissioner of Patents and Trademarks